United States Patent [19]

Oxenrider et al.

[11] 4,321,403

[45] Mar. 23, 1982

[54] N-METHYLPYRROLIDONE SOLVENT IN ESTERIFICATION OF CARBOXYBENZENES

[75] Inventors: Bruce C. Oxenrider, Florham Park; Frank Mares, Whippany, both of N.J.

[73] Assignee: Allied Corporation, Morristown, N.J.

[21] Appl. No.: 44,880

[22] Filed: Jun. 4, 1979

[51] Int. Cl.$^3$ .................. C07C 67/08; C07C 67/26
[52] U.S. Cl. ............................. 560/87; 252/8.6; 252/8.9; 560/83; 560/84
[58] Field of Search ............... 560/87, 84, 93, 94, 560/111, 83

[56] References Cited

U.S. PATENT DOCUMENTS

| | | | |
|---|---|---|---|
| 3,391,179 | 7/1968 | Hallander et al. | 560/87 |
| 3,547,861 | 12/1970 | Anello et al. | 260/89.5 |
| 4,125,733 | 11/1978 | Sandler | 560/87 |
| 4,134,839 | 1/1979 | Marshall | 560/87 |

FOREIGN PATENT DOCUMENTS 1543081  3/1979  United Kingdom .

Primary Examiner—Vivian Garner
Attorney, Agent, or Firm—A. M. Doernberg; R. A. Harman

[57] ABSTRACT

An anhydride of a carboxybenzene is esterified in solution by a fluorinated alcohol, using N-methylpyrrolidone solvent. In particular, pyromellitic dianhydride in N-methylpyrrolidone solvent is esterified to the diester/diacid by 2-(n-perfluoroalkyl)ethanols having six to twelve carbon atoms in the perfluoroalkyl groups, and the reaction mixture containing the dissolved diester/diacid is admixed with an oxirane compound of the group ethylene oxide, epichlorohydrin and glycidol whereby the carboxyl groups are esterified in the N-methylpyrrolidone solvent by reaction with oxirane groups.

5 Claims, No Drawings

N-METHYLPYRROLIDONE SOLVENT IN ESTERIFICATION OF CARBOXYBENZENES

DESCRIPTION

Background of the Invention

This invention relates to esterification of carboxybenzenes, especially such esterification in solution by contact of an anhydride of a carboxybenzene with a fluorinated alcohol. Such esterification process is broadly known, and is especially useful in preparation of compounds capable of imparting oil and/or water repellency to textiles, especially to fibers of PET and nylon.

In particular, as disclosed in British Pat. No. 1,543,081 to our assignee, published Mar. 28, 1979 very useful agents for imparting oil and water repellency are obtained by contacting in solution an anhydride of a carboxybenzene especially pyromellitic dianhydride and various fluorinated alcohols to form the corresponding fluorinated ester/acid and by then contacting in solution the resulting fluorinated ester/acids with an oxirane compound of the group ethylene oxide, epichlorohydrin, or glycidol. Thus, specifically, pyromellitic dianhydride is esterified in Example 5 Part G of BP No. 1,543,081 by a mixed perfluoro-n-hexyl-, perfluoro-n-octyl-, or perfluoro-n-decylethanol in dry dimethylformamide ("DMF") solvent; the resulting diester/diacid is isolated; and the diester/diacid is admixed with epichlorohydrin in dry acetonitrile using a little pyridine as catalyst to bring about an esterification reaction of the carboxyl groups of the diester/diacids with the oxirane group of epichlorohydrin.

More generally, esterification of anhydride by fluorinated alcohol has been disclosed using solvents such as benzene, pyridine, quinoline, nitrobenzene, dimethylaniline, Decalin and 1,1,2-trifluoro-1,2,2-trichloroethane; in particular for anhydrides of acrylic compounds—U.S. Pat. No. 3,547,861 of Dec. 15, 1970 to Anello et al. at column 4, lines 1–41.

SUMMARY OF THE INVENTION

We have found that by use of "NMP" (N-methylpyrrolidone) solvent for esterification of "PMDA" (pyromellitic dianhydride) by fluorinated alcohol it becomes unnecessary to isolate the diester/diacid product or to use a different solvent for esterification of the diester/diacid with an oxirane compound. Instead, the diester/diacid can simply be admixed as such, with addition of a little basic catalyst such as an organic base, with the oxirane compound and when reaction is complete, the resulting pyromellitate can be precipitated by adding the reaction mixture to cold water, and worked up by water washing and drying under vacuum. The resulting product appears fully comparable in the oil repellency conferred, and in resistance of the resulting repellency to laundering, to the similar products described in the above British Patent and is superior in comparative testing against a like product similarly made using DMF solvent (also without isolation of the intermediate).

Thus the invention includes a process for esterification of a carboxybenzene which comprises contacting an anhydride of a carboxybenzene selected from the group consisting of hemimellitic acid, trimellitic acid, tetracarboxybenzenes (e.g. promellitic acid), pentacarboxybenzenes and mellitic acid with a fluorinated alcohol having a straight chain, branched chain or cyclic fluorinated moiety of 2–20 carbons attached to a hydroxy substituted hydrocarbon moiety of 2–20 carbons in a solvent consisting essentially of N-methylpyrrolidone.

We believe favorable results will be obtained by use of NMP solvent in esterification via reaction of anhydrides of carboxybenzenes, generally with fluorinated alcohols, generally; provided the anhydride and the alcohol each has substantial solubility in NMP at a temperature below the decomposition temperature of the reactants and solvent.

DETAILED DESCRIPTION

Anhydrides of carboxybenzenes believed to be useful in our process, in addition to pyromellitic dianhydride, are anhydrides of hemimellitic acid and trimellitic acid; those from tetracarboxybenzenes including prehnitic acid and mellophanic acid; those of the pentacarboxybenzenes; and those of mellitic acid.

Numerous fluorinated alcohols are disclosed in the prior art, for example in BP No. 1,543,081 and U.S. Pat. No. 3,547,861 above cited, all of which alcohols we believe to be operative in our process. These include fluorinated alcohols having straight chain, branched chain and cyclic fluorinated moieties attached to a hydroxy substituted hydrocarbon moiety, each moiety having between 2 and 20 carbon atoms, especially such alcohols in which the fluorinated moiety has between 3 and 12 carbon atoms and the hydrocarbon moiety has between 2 and 12 carbon atoms. The fluorinated moiety can be perfluorinated and can alternatively be partially fluorinated, for example having a terminal hydrogen atom. Also either or both the fluorinated moiety and the hydroxyl substituted moiety can contain substituents such as chlooro, bromo or iodo; and the same applies to the coreactant, the anhydride of a carboxybenzene.

specific suitable fluorinated alcohols for esterification of carboxybenzenes by our process include the (perfluoroalkyl)ethanols and the (perfluoroalkyl) propanols having three to twelve carbon atoms in the perfluoroalkyl groups; and the (omega-perfluoroisopropoxyperfluoroalkyl)ethanols, and the propanol homologues thereof, having two to ten carbon atoms in the perfluoroalkyl groups. Preferred alcohols of the above group, in view of their availability and effectiveness in producing esters with the desired properties, are mixtures consisting essentially of 2-(n-perfluoroalkyl)ethanols having six to twelve carbon atoms in the perfluoroalkyl groups. Temperature and pressure used for the reaction are not critical and will be chosen to give a satisfactory reaction rate while avoiding decomposition of the products such as decomposition due to hydrolysis.

A catalyst is not necessary in the reaction of the fluorinated alcohol with the anhydride but conventional catalysts for this reaction such as bases or Lewis acids can be used if desired. A catalyst is helpful in the reaction of the oxirane compound with the carboxyl group of the ester/acid, such as especially an organic base.

EXAMPLES

The preparations below were carried out as follows:

Equipment: 100 mL 3-neck flask (glass) fitted with stirring bar, thermometer, water condenser and inlet tube for nitrogen gas.

Procedure: The flask and fittings, after oven drying and cooling in a desiccator, were charged with a mixture of 2-(n-perfluoroalkyl)ethanols having six to twelve carbon atoms in the perfluoroalkyl groups, and PMDA (pyromellitic dianhydride) in 2:1 mol ratio of alcohol:PMDA and with solvent at about 1:1 weight ratio with the alcohol. The flask was immersed in a heating bath at the temperatures shown in the Examples and a slow stream of nitrogen was passed through the flask to maintain a dry atmosphere.

When sampling of the reaction mixture for unreacted alcohols (by gas chromatography) indicated not over about 1% unreacted alcohols, epichlorohydrin and a small amount of organic base catalyst were added to the reaction mixture at mol ratio 6:1 of epichlorohydrin: starting PMDA. The reaction mixture was periodically sampled for unreacted epichlorohydrin (by titration with HBr in glacial acetic acid using crystal violet indicator) and also periodically sampled for the starting alcohols to verify that no substantial hydrolysis of ester or replacement of alcohol by chlorohydrin or like side reaction had occurred. (Final unreacted alcohol analysis was not over about 5–6%).

When the reaction with epichlorohydrin was found to be essentially complete, the product was precipitated by stirring the reaction mixture with about 10–15 volumes of cold water and washed with water, three times, in the same manner; and then dried under vacuum at room temperature.

The resulting products were examined by NMR, and tested for percent unreacted alcohols as before. Using the procedure of British Pat. No. 1,543,081 Example 10, the products were applied to nylon-6 cloth, which was annealed at 140° C. and at 155° C. and tested for oil repellency and for resistance of oil repellency to laundering, as in BP No. 1,543,081.

Results using N-methylpyrrolidone solvent and for comparison, using DMF solvent in the same procedure, are shown in the table which follows.

In the table, the epichlorohydrin "remaining," (per titration with HBr) levels off at about 70%–73% of that originally added; whereas theoretically this figure should be 66.67% (since epichlorohydrin is added in 3-fold the stoichiometrically required amount). The discrepancy has been found to be due to presence of the NMP solvent. When instead of the HBr titration for remaining epichlorohydrin, a titration is performed for unreacted carboxyl groups (potentiometric titration by alcoholic KOH), completion of the reaction of carboxyl with epichlorohydrin under the conditions of the table is confirmed, by absence of remaining carboxyl groups.

TABLE

| Example 1 Wgt. of reactant (g) Alc. | PMDA | Catalyst added and moles per 100 moles alcohol used | Temp. (°C.) used | Reaction time from start (hr) | % Initial reactant found, & % completion | Initial analysis of mixed alcohols (meq. of OH/g) |
|---|---|---|---|---|---|---|
| 28.3 | 6.66 | 2,6-lutidine 0.105 mL 1.5 mole % | 55° | 2:00 | Alc. <0.4% (ca/80% complete) | 2.16 |
| | | | | | % Initial reactants, found: | |
| | | | | | Alcohols | Epichlorohydrin |
| Epichlorohydrin 16.97 g added to reaction mixture. | | | | 2:35 5:40 | <0.4% (100% complete reaction) | 90% Remaining |
| | | | | 8:55 | | 76.5% Remaining |
| | | | | 10:55 | | 73% Remaining |
| | | | | 12:10 | | 73% Remaining |
| | | | | (Stored in refrigerator overnight) | | |
| | | | | 15:40 | | 73% Remaining |
| | | | | 18:10 | | 71.5% Remaining |
| | | | | 19:55 | | 70% Remaining |
| | | | | 20:40 | | 71% Remaining |
| | | | | (Left standing overnight at room temperature under nitrogen stream) | | |
| | | | | | <0.4% | 70.5% Remaining |

Product precipitated in water, washed, and vacuum dried, room temp. about 80 hr. Testing for oil repellency and laundering resistance conferred on nylon-6-cloth:

| | Oil Repellency | | | |
|---|---|---|---|---|
| | Ex 1: (Using NMP Solv.) | | Comparison: (using DMF solvent) | |
| HL Cycles | 140° C. Anneal | 155° C. Anneal | 140° C. Anneal | 155° C. Anneal |
| 0 | 7 | 7 | 6 | 6 |
| 1 | 7 | 7 | 6 | 6 |
| 2 | 6+ | 7 | 5 | 5 |
| 3 | 6 | 6 | 5 | 5 |
| 4 | 6 | 6 | 5 | 5 |
| 5 | 6 | 6 | 4 | 5 |
| 6 | 5 | 6 | 4 | 4 |
| 7 | 5 | 6 | 4 | 4 |
| 8 | 5 | 5 | 4 | 2 |
| 9 | 5 | 5 | 2 | 2 |
| 10 | 5 | 5 | 1 | 1 |
| 11 | 4 | 4 | — | — |

Remarks: Both the product of Ex. 1 and the comparison product showed after the drying step, a content of starting alcohols (by GC) of about 5%–6%, possibly to be attributed to action of chlorohydrin on the diester intermediate product. The titration for epichlorohydrin in the comparison test indicated slightly less than the theoretical amount of as remaining at the point of completion. The discrepancy is attributed to the presence of the added catalyst. The alcohols found at this point amounted to 2.99% of the initially added quantity.

EXAMPLE 2

This example was carried out essentially as for Example 1 except that in the reaction of the alcohols with PMDA, the bath temperature was 45° C. and the catalyst was 3 mole % of triethylamine; and in the reaction with epichlorohydrin the bath temperature was 60° C. After a total reaction time of 11:30 hours, the percent of initially added alcohols found was 1.7% (vs. <0.5% at start of epichlorohydrin addition) and percent of initially added epichlorohydrin found was 73%, representing essentially complete reaction.

The comparison test using dimethylformamide solvent, at the point of completion of reaction with epichlorohydrin showed 2.2% of alcohols based on the initial quantity charged.

The results of testing the product of Example 2 and comparison product for oil repellency and laundering resistance conferred on nylon-6 cloth were as follows:

|  | Oil Repellency | | | |
| --- | --- | --- | --- | --- |
| | Ex 2: (Using NMP Solv.) | | Comparison: (Using DMF solvent) | |
| HL Cycles | 140° C. Anneal | 155° C. Anneal | 140° C. Anneal | 155° C. Anneal |
| 0 | 7 | 7 | 6 | 6 |
| 1 | 6 | 6 | 6 | 6 |
| 2 | 6 | 6 | 6 | 6 |
| 3 | 6 | 6 | 6 | 5 |
| 4 | 6 | 6 | 6 | 5 |
| 5 | 6 | 6 | 5 | 5 |
| 6 | 6 | 6 | 4 | 4 |
| 7 | 5 | 5 | 4 | 4 |
| 8 | 5 | 5 | 4 | 2 |
| 9 | 4 | 5 | 2 | 2 |
| 10 | 5 | 5 | — | — |
| 11 | 4 | 5 | — | — |
| 12 | 3 | 4 | — | — |
| 13 | 2 | 3 | — | — |

In the NMR spectrograms the comparison products from Examples 1 and 2 each shows, by presence of one or more minor peaks (not observed in the products of the invention), the presence of one or more impurities. Likewise the high pressure liquid chromatogram of Product 2 vs. the comparison product indicates greater purity of the product made using N-methylpyrrolidone solvent vs. DMF solvent, when the intermediate diester of fluorinated alcohol is not isolated.

We claim:

1. A process for esterification of a carboxybenzene which comprises contacting an anhydride of a carboxybenzene selected from the group consisting of hemimellitic acid, trimellitic acid, tetracarboxybenzenes, pentacarboxybenzenes and mellitic acid with a fluorinated alcohol having a straight chain, branched chain or cyclic fluorinated moiety of 2–20 carbons attached to a hydroxy substituted hydrocarbon moiety of 2–20 carbons or mixtrues thereof in a solvent consisting essentially of N-methylpyrrolidone.

2. Process of claim 1 wherein selected from is a (perfluoroalkyl)ethanol or (perfluoroalkyl)propanol having three to twelve carbon atoms in the perfluoroalkyl groups; or an (omega-perfluoroisopropoxyperfluoroalkyl) ethanol or- propanol having two to ten carbon atoms in the perfluoroalkyl groups or mixtures thereof.

3. Process of claim 2 wherein said fluorinated alcohol is a mixture consisting essentially of 2-(n-perfluoroalkyl) ethanols having six to twelve carbon atoms in the perfluoroalkyl groups.

4. Process of claim 1 or 3 wherein the compound esterified is pyromellitic dianhydride.

5. Process of claim 4 wherein the reaction mixture obtained, containing dissolved diester of pyromellitic acid, is admixed with an oxirane compound of the group ethylene oxide, epichlorohydrin, and glycidol whereby the carboxyl groups are esterified by reaction thereof with oxirane groups.

* * * * *

UNITED STATES PATENT AND TRADEMARK OFFICE
CERTIFICATE OF CORRECTION

PATENT NO. : 4,321,403
DATED : March 23, 1982
INVENTOR(S) : Bryce C. Oxenrider and Frank Mares It is certified that error appears in the above-identified patent and that said Letters Patent are hereby corrected as shown below:

Title page, first inventor's name "Bruce" C. Oxenrider should read --Bryce-- C. Oxenrider.

Col. 2, line 34, "chlooro" should read --chloro--;
       line 36, "specific" should read --Specific--

Col. 6, line 16, "mixtrues" should read --mixtures--;
       line 18, "selected from is" should read --said fluorinated alcohol is selected from--

Signed and Sealed this

Twentieth Day of July 1982

[SEAL]

Attest:

GERALD J. MOSSINGHOFF

Attesting Officer    Commissioner of Patents and Trademarks